United States Patent [19]

Dormandy, Jr. et al.

[11] Patent Number: 5,746,734

[45] Date of Patent: *May 5, 1998

[54] INTRODUCER CARTRIDGE FOR DELIVERING AN EMBOLIZATION DEVICE

[75] Inventors: Ray H. Dormandy, Jr., San Bruno; Marcelyn A. Berlo, San Francisco; David J. Paul, Pleasanton, all of Calif.

[73] Assignee: International Therapeutics Corporation, Fremont, Calif.

[*] Notice: The term of this patent shall not extend beyond the expiration date of Pat. No. 5,382,260.

[21] Appl. No.: 527,186

[22] Filed: Sep. 12, 1995

Related U.S. Application Data

[63] Continuation of Ser. No. 243,197, May 16, 1994, Pat. No. 5,476,472, which is a continuation-in-part of Ser. No. 969,008, Oct. 30, 1992, Pat. No. 5,382,260.

[51] Int. Cl.⁶ ............................................. A61B 19/00
[52] U.S. Cl. ............................................. 606/1
[58] Field of Search ................... 606/1, 151, 190–200, 606/108; 604/164, 264

[56] References Cited

U.S. PATENT DOCUMENTS

| | | | |
|---|---|---|---|
| 4,317,445 | 3/1982 | Robinson | 604/264 |
| 4,781,703 | 11/1988 | Walker et al. | 604/264 |
| 4,950,257 | 8/1990 | Hibbs et al. | 604/264 |
| 5,382,260 | 1/1995 | Dormandy et al. | 606/108 |

Primary Examiner—Glenn K. Dawson
Attorney, Agent, or Firm—Morrison & Foerster

[57] ABSTRACT

An introducer cartridge for an embolization device for use with a delivery catheter having a proximal end with a hub mounted thereon and having a conical recess therein. The introducer cartridge includes a flexible elongate tubular member formed of a clear plastic and has a flow passage extending therethrough and has proximal and distal extremities. The distal extremity is tapered and a hub formed of clear plastic is secured to the proximal extremity of the flexible elongate tubular member. The hub of the introducer cartridge has a conical recess therein having proximal and distal extremities. The distal extremity of the conical recess has a diameter which is slightly less than the diameter of the flow passage in the elongate tubular member.

4 Claims, 4 Drawing Sheets

INTRODUCER CARTRIDGE FOR DELIVERING AN EMBOLIZATION DEVICE

CROSS REFERENCE TO RELATED APPLICATION

This is a continuation of application Ser. No. 08/243,197 filed May 16, 1994, now U.S. Pat. No. 5,476,472; which is a continuation-in-part of application Ser. No. 07/969,008 filed Oct. 30, 1992, now U.S. Pat. No. 5,382,260.

FIELD OF THE INVENTION

This invention relates to an embolization device and an apparatus including an introducer cartridge, a delivery catheter and method for delivering the same in an intravascular procedure.

BACKGROUND OF THE INVENTION

Embolization devices have heretofore been provided which can be used in intravascular procedures. Typically such prior art devices have used coils with fibers attached to the coils. In certain embodiments, the fibers are merely retained by friction between the windings of the coil making it possible for the fibers to become separated from the coil. In other embodiments, the fibers have been tied by knots to the windings of the coil, making the exterior surface of the coil lumpy or bumpy.

Apparatus heretofore provided for delivering such embolization coils to the site have included introducer cartridges for carrying the embolization coils and typically have been in the form of stainless steel tubes serving as shipping containers and also serving as introducers for the coils when they are being introduced into a delivery catheter. It has been found that such stainless steel cartridges do not interface well with the delivery catheter hub making it difficult to introduce the embolization coil from the stainless steel tube and traverse the part of the hub of the delivery catheter before entering the passage of the delivery catheter. There is a need for the introducer cartridge to be transparent along substantially its entire length to permit viewing of the embolization coil which heretofore has not been possible. Also in delivery catheters the hub has usually been opaque making viewing of the interior lumen difficult. There is therefore a need for a new and improved embolization device and an introducer cartridge and a delivery catheter as a part of an apparatus and method for delivering the embolization device to the desired site in the intravascular system.

SUMMARY AND OBJECTS OF THE INVENTION

In general, it is an object of the invention to provide an embolization device and an apparatus and method for delivering the same to an intravascular site.

Another object of the invention is to provide an embolization device with the fibers carried thereby being securely attached thereto without providing bumpiness to the exterior surface of the embolization device.

Another object of the invention is to provide an introducer cartridge for use in the apparatus and method which has a distal extremity which is tapered to permit it to proximally engage the catheter hub to maintain the alignment of the introducer cartridge with the catheter hub.

Another object of the invention is to provide an introducer cartridge of the above character in which the distal extremity is tapered to facilitate deeper penetration of the introducer cartridge into the catheter hub.

Another object of the invention is to provide an introduction cartridge of the above character in which the friction fit between the introducer cartridge and the delivery catheter hub maintains the alignment of the distal extremity of the cartridge with the internal diameter or passage of the catheter attached to the catheter hub.

Another object of the invention is to provide an introducer cartridge of the above character which is transparent and a delivery catheter of which at least the hub is transparent so that movement of the embolization device in the same can be visualized.

Another object of the invention is to provide an introducer cartridge of the above character which is provided with wings which are positioned so as to provide the least interference with visualization of the entire length of the lumen in the introducer cartridge.

Another object of the invention is to provide an introducer cartridge of the above character in which a stylet can be utilized to advance the embolization device out of the introducer cartridge.

Additional objects and features of the invention will appear from the following description in which the preferred embodiments are set forth in detail in conjunction with the accompanying drawings.

In general, the embolization device is comprised of an elongate coil having a plurality of turns and formed of a metal which is relatively opaque to x-rays. At least one group of a plurality of fibers is secured to the coil. The group of fibers has an intermediate portion and first and second end portions. The intermediate portion is looped about one of the turns to form a loop which encircles said one turn and so that the first and second end portions extend interiorly of the coil and then outwardly from the interior of the coil through two adjacent turns on opposite sides of the loop so that the first and second ends are free to permit the fibers in the first and second ends to move about.

DETAILED DESCRIPTION OF THE PREFERRED EMBODIMENTS

Figure 1:
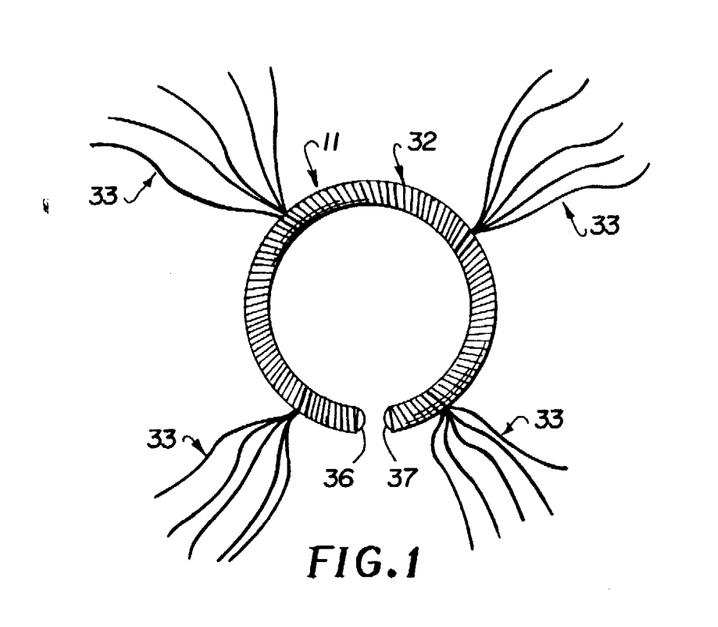
FIG. 1 is a plan view of an embolization device which has a "C" or circular shape incorporating the present invention.
Figure 2:
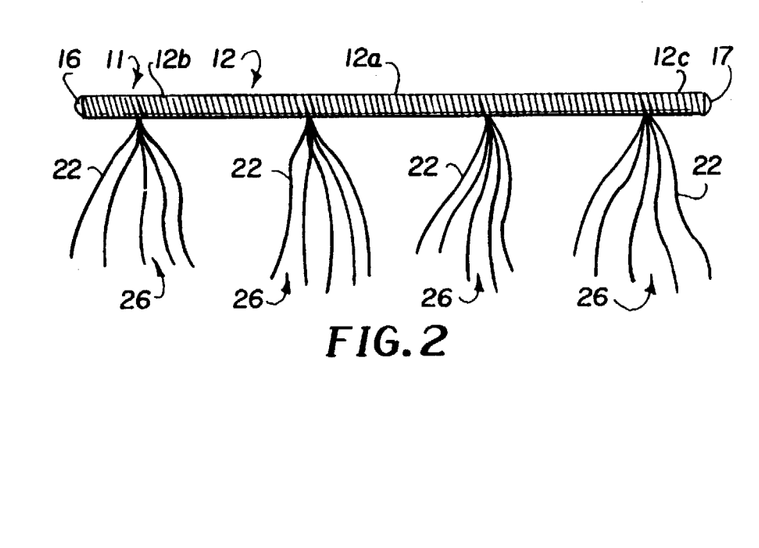
FIG. 2 is a plan view of another embodiment of an embolization device incorporating the present invention which is in straight.

More particularly as shown in FIGS. 1 and 2 in the drawings, the embolization device 11 is comprised of a coil 12. The coil 12 consists of a plurality of helically wound turns 13. The coil 12 is formed of a metal which is relatively opaque to x-rays and may be made of a material such as stainless steel, copper, gold, or platinum alloys. Because of their higher radiopacity, a platinum alloy is preferred, as for example a platinum alloy 479 supplied by Sigmond Cohn. The coil 12 can have a primary outside diameter ranging from 0.2 millimeters to 1.3 millimeters and can have a length ranging from 2 millimeters up to 90 millimeters. The wire utilized for forming the coil can have a suitable diameter ranging from 0.002" to 0.006". For a coil having an outside diameter of 0.4 millimeters, the wire utilized can have a diameter of 0.003".

Typically, the bulk material from which the coil is made is shipped in a primary winding of the desired wire size and outside diameter. The bulk material may then be wound into a secondary coil with secondary outside diameters ranging from 2 millimeters to 10 millimeters. The coil 12 is then cut into appropriate lengths for making coils in accordance with the present invention. Typically, the coils are cut to a length of 1 millimeter longer than the desired length to allow for loss during melting of the ends as hereinafter described. The coil 12 is provided with an intermediate portion 12a and first and second end portions 12b and 12c. The coil 12 can be placed in a fixture (not shown) and then the first end portion 12b can be advanced into a torch flame until the end of the coil melts into a smooth, rounded end 16. The fixture can then be reversed and the other end portion 12c advanced into the flame to form a rounded end portion 17 as shown in FIG. 2 of the drawings. After the rounded ends 16 and 17 have been formed, the coil 12 can be ultrasonically cleaned.

Thereafter, the coil can be placed in another fixture, as for example a tube which is then placed in a pin vise for holding the same for fiber attachment. For this purpose, a suitable length of yarn, as for example 10" is cut from a coil of the yarn. The yarn is formed of a suitable synthetic medical grade material such as Dacron. The yarn is comprised of a plurality or groups 21 of filaments or fibers 22 of a suitable size such as 30 Denier. The group 21 of fibers 22, in other words, the cut-off piece of yarn is then taken and gently pushed between turns 13 in a predetermined location in accordance with the design for the embolization device. For example, only one group of fibers can be utilized or a plurality of groups of fibers can be utilized which are spaced a suitable distance apart, as for example 2 millimeters so that the number of groups of fibers is dependent upon the length of the coil. Each group 21 is pressed into the coil 12 between two adjacent turns 13. Then, by holding one end of the yarn or group, the other end is brought back through the coil and then successively advanced through two additional turns of the coil. The yarn or group 21 is then brought back and looped over the last turn which has just been passed and then progressively advanced through two additional turns and then brought back to the position shown in FIG. 3. Thus, it can be seen that the yarn or group of fibers 21 is provided with an intermediate portion 21a and first and second ends 21b and 21c. The group 21 of fibers, after it has been looped about one of the turns of the coil 12 to form a loop 23 that encircles the turn 13 extends from the intermediate portion 21a in opposite directions interiorly of the coil for at least one additional turn and then outwardly from the interior of the coil between adjacent turns. In this way, the ends 21b and 21c of the group 21 are free to form something like tufts 26 extending along one side of the coil 12. The loop 23 serves as the sole means for retaining the group 21 of fibers 22 on the coil 12.

Figure 3:
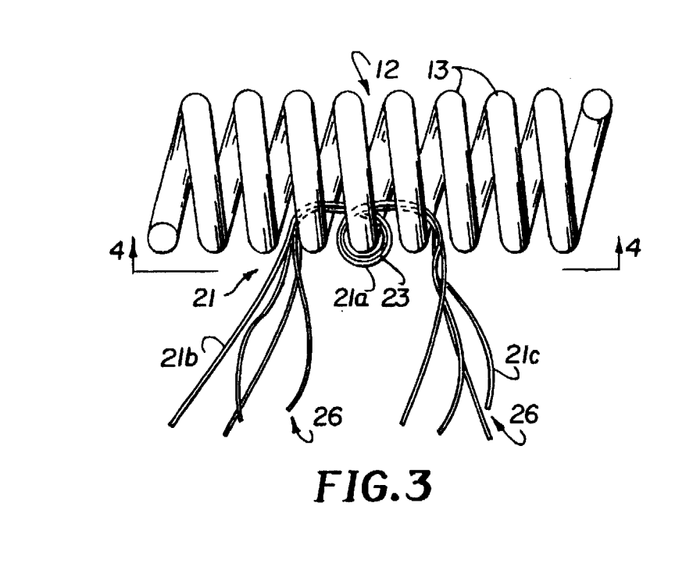
FIG. 3 being an enlarged partial side elevational view of a portion of an embolization device incorporating the present invention showing the manner in which groups of fibers are secured to the coil.
Figure 4:
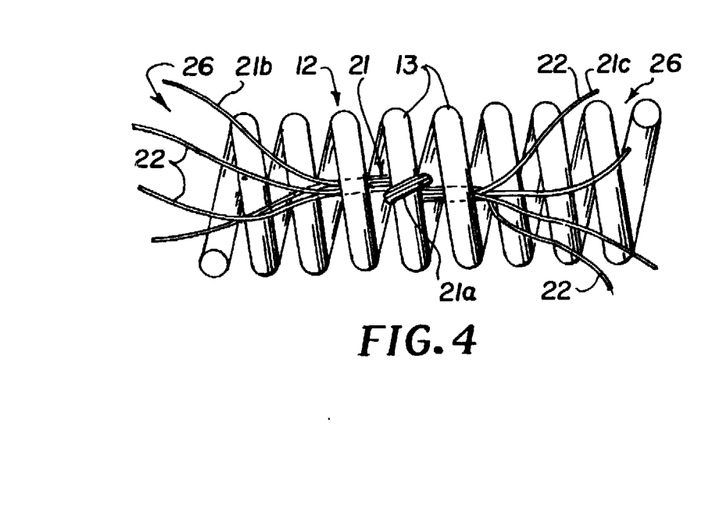
FIG. 4 is a view looking along the line 4—4 of FIG. 3.

As can be seen in FIG. 1, when the coil 12 is of a suitable length, additional groups of fibers 21 and can be spaced apart longitudinally of the coil and can be secured in the same manner as hereinbefore described and as shown in FIGS. 3 and 4. Thus, the tufts 26 spaced apart a suitable distance, as for example approximately 2 millimeters along the length of the coil 12. By way of example, the embolization device 11 can have a coil external diameter of, for example, 2 millimeters and an extended length of 6 millimeters.

In addition to the straight shape for the coil 12 shown in FIG. 2, a curved coil 32 can be, provided which is circular or C-shaped as shown in FIG. 1. This C-shaped coil is formed by taking the primary winding 12 and preforming a secondary winding to form the C-shaped coil 32 on a coil-winding apparatus. A tension line is place inside the primary winding 12 and together are wound by a computer-controlled machine onto a mandrel of specified diameter. The secondary winding is then removed from the mandrel and the shape is set in a furnace at a specified time and temperature. The tension line is then removed from the secondary winding. Tufts 33 are provided on the coil 32 and are formed in the same manner as the tufts 26 shown in FIG. 2. As shown, they are provided on the exterior circumferential surface of the coil and are spaced apart a suitable distance, as for example the 2 millimeters utilized in conjunction with the tufts in FIG. 2. The coil 32 is provided with rounded ends 36 and 37 formed in the same way as the ends 16 and 17 for the coil 12 in FIG. 2.

Figure 5:
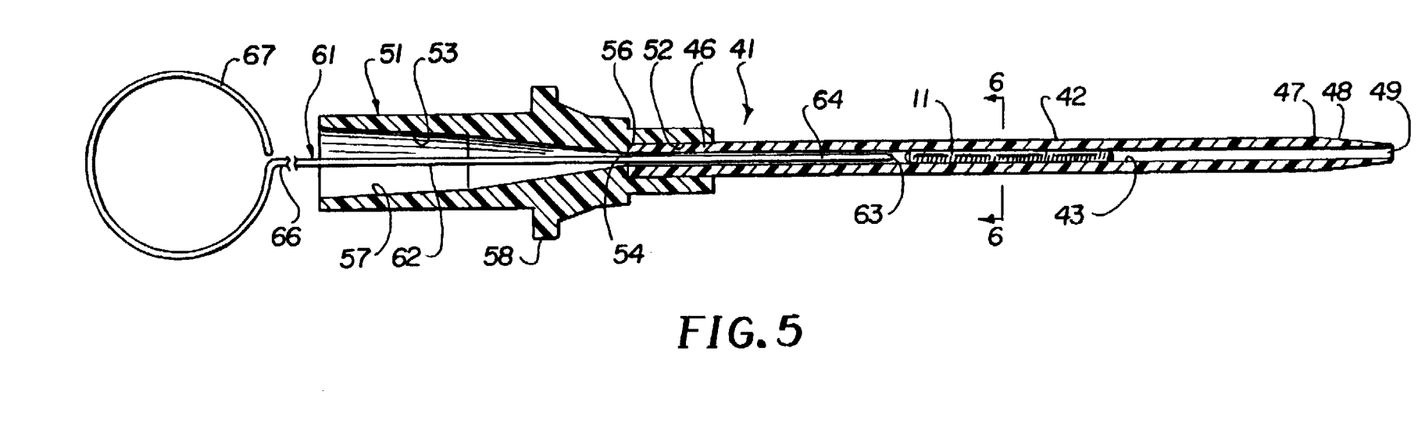
FIG. 5 is a cross-sectional view of an introducer cartridge with coil and stylet for introducing the embolization device intravascularly.
Figure 6:
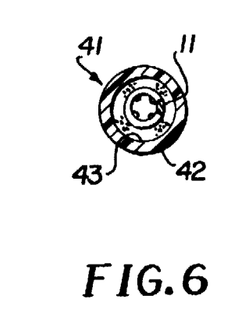
FIG. 6 is a cross-sectional view looking along the line 6—6 of FIG. 5.

The C-shaped embolization device 32 as shown in FIG. 1 is shown in its at rest or normal position. The embolization device can be in the C-shaped form which is shown in FIG. 1 or, alternatively, it can be in a straight form such as shown in FIG. 2. However, it is provided loaded into a cartridge 41. The C-shaped coil 32 can be straightened to the conformation as shown in FIG. 2 and then it can be loaded into the introducer cartridge 41. The introducer cartridge 41 as shown in FIGS. 5 and 6 consists of an elongate tubular member 42 formed of a clear transparent plastic such as a radiation sterilizable polycarbonate. It is provided with the passage 43 extending therethrough. It can have a suitable size, for example, an inside diameter of 0.023" and an outside diameter of 0.060". Even though the tubular member is bendable, it is still relatively rigid so that it can be utilized as an introducer as hereinafter described. The elongate tubular member 42 is provided with proximal and distal extremities 46 and 47. The distal extremity is provided with a tapered tip 48. The introducer cartridge 41 can have a suitable length ranging from 3" to 5", as for example 4.875". The tip 48 can have a suitable length such as 0.3". The tip 48 is tapered with the outside diameter decreasing from the 0.060" for the remaining portion of the tubular member 42 down to approximately 0.030" with the distal extremity of the tip of 48 being rounded at 49.

A hub 51 is mounted on the proximal extremity 46 of the elongate tubular member 42 and is also formed of the clear radiation sterilizable polycarbonate. The hub 51 is provided with a cylindrical recess 52 which is sized to receive the proximal extremity 46 of the elongate tubular member 42. The cylindrical recess 52 opens into a tapered conical recess 53 which has a proximal extremity sized so that its interior diameter at 54 of approximately 0.020" is slightly less than or equal to the interior diameter of 0.023" of the passage 43 in the elongate tubular member 42. The proximal extremity 46 of the elongate tubular member 42 abuts a shoulder 56 provided in the shoulder 51. The shoulder 56 extends over or aligns with the proximal extremity of the elongate tubular member 42. The conical recess 53 can have a suitable length, for example 0.44". The conical recess 53 subtends a suitable angle, as for example approximately 9° from the horizontal and adjoins another conical recess 57 which subtends an angle of approximately 3°. The conical recess 57 can have a suitable length as, for example 0.356". The hub 51 is also provided with a circular flange 58 approximately midway of the conical recess 53 and extending radially or outwardly therefrom. The flange 58 may be provided with a flat (not shown).

As can be seen in FIG. 5, the embolization device 11 is disposed within the passage 43 of the introducer cartridge 41. Because of the small size, the embolization device 11 is typically introduced into the introducer cartridge 41 under a microscope. A tweezer (not shown) is utilized to pick up the embolization device 11 and inserting it into the conical recess 57 and then advancing it into the conical recess 53 and over the shoulder 56 into the passage 43. Thereafter, it can be introduced further into the passage 43 by the use of a stylet 61 (see FIG. 5). The stylet 61 can be of a suitable length such as 8.375" and can be formed of elongate wire 62 of a suitable diameter such as 0.018". It is provided with a rounded tip 63 on its distal extremity 64. The proximal extremity 66 is formed into a circle of the suitable diameter, as for example ¼", which serves as a handle 67 for using the same. By grasping the handle 67, the assembler can introduce the embolization device 11 further into the passage 43 where it will be protected and remain therein until the embolization device is ready to be used as hereinafter described.

The stylet 61 can then be removed and packaged with the introducer cartridge 41 for later use in a sterile package (package not shown).

Let it be assumed that it is desired to use the embolization device 32 and the introducer cartridge 41 in connection with a medical procedure and apparatus to inhibit or stop hemorrhaging occurring in a vessel of the patient, that is, blood is flowing in an undesired manner and it is desired to form a clot of the blood in the vessel. By way of example, the procedure can be utilized in connection with a brain hemorrhage. However, it should be appreciated that the procedure can be utilized in other small vessels in the body to form a clot or embolism in a desired location.

Let it be assumed that a cut has been made in the femoral artery of the patient and a femoral sheath (not shown) of the conventional type has been placed in the femoral artery of the patient. The physician performing the procedure then takes apparatus which includes a conventional guide wire, as for example a 0.038" diameter guide wire 71. The guide wire 71 is provided with a distal extremity which is very flexible. This distal extremity is introduced into the sheath and then advanced through the femoral artery under fluoroscopy through the aortic arch and then through the carotid artery in the neck and then advancing into the desired vessel in the brain to a location or site in which it is desired to place a catheter for forming an embolism in accordance with the present invention.

As soon as the guide wire 71 is in place, a catheter assembly 76 (see FIG. 7) forming a part of the apparatus is utilized which consists of an introducer catheter 77 with a guiding catheter 78 disposed in the same. This catheter assembly 76 is advanced over the guide wire 71 as hereinafter described.

Figures 7, 8, 9:
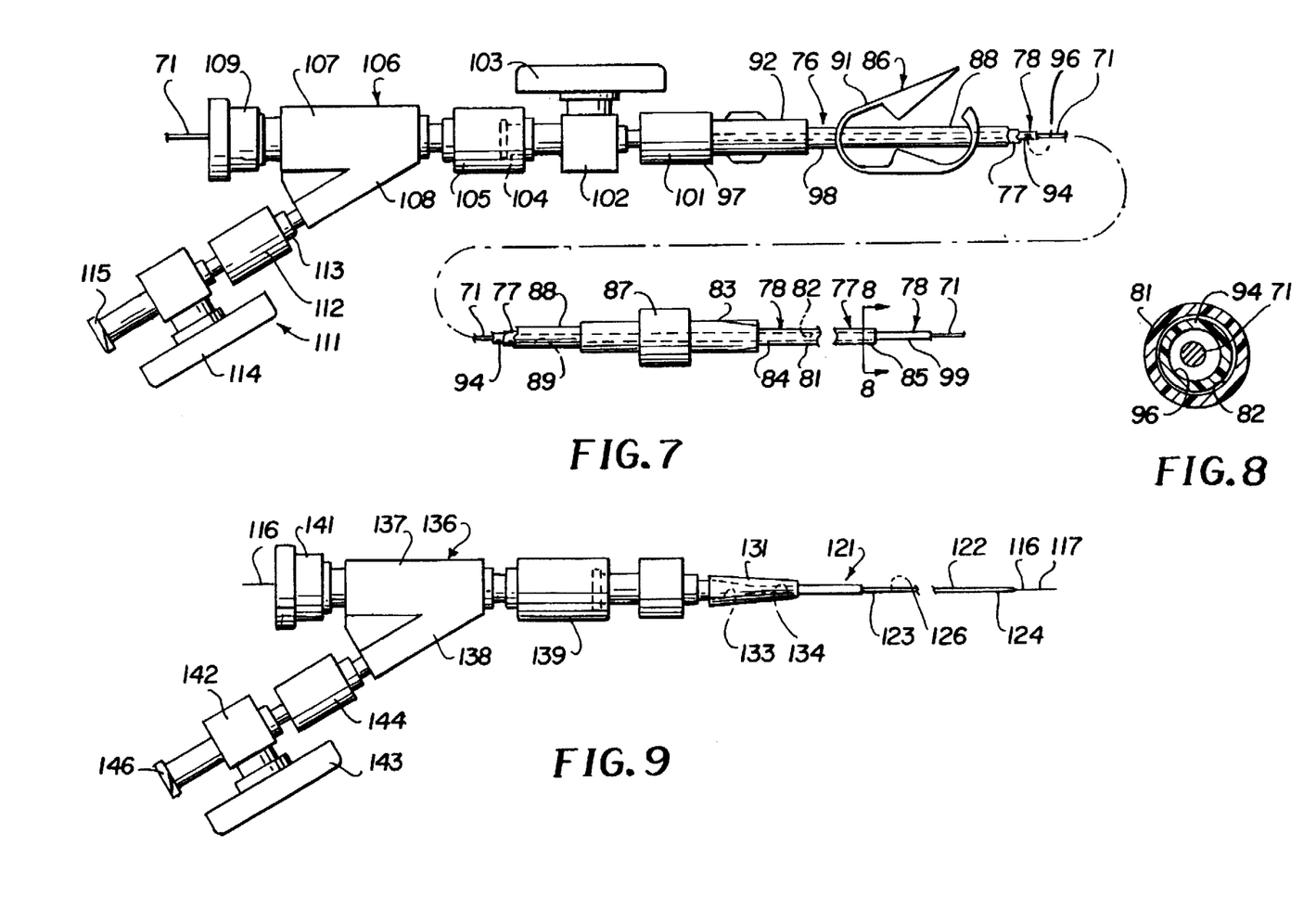
FIG. 7 is a side elevational view showing a catheter assembly consisting of an introducer catheter and a guiding catheter used as the apparatus for delivering the embolization device to the intravascular site.
FIG. 8 is a cross sectional view taken along the line 8—8 of FIG. 7.
FIG. 9 is a side elevational view of the delivery catheter used in the apparatus.

The introducer catheter 77 is comprised of a flexible elongate tubular member 81 with a flow passage 82 therein. The introducer catheter 77 can be of a suitable size, as for example 7.3 French and having a length of 90 centimeters and a flow passage 82 with an inside diameter of 0.070". A female Luer fitting 83 is mounted on the proximal extremity 84 of the flexible elongate tubular member 81. The flexible elongate tubular member 81 is provided with the distal extremity 85. The female Luer fitting 83 is releasably attached to a clamp assembly 86. The clamp assembly 86 consists of a mating Luer fitting 87 of a conventional type and has a relatively short flexible tubular member 88 mounted therein with a suitable outside diameter such as ³⁄₁₆" and having a flow passage 89 therein of a suitable diameter such as ⅛". The passage 89 is adapted to be clamped to a closed position by a releasable clamp 91 of a conventional type disposed on the tubular member 88. A female Luer fitting 92 is provided on the other end of the tubular member 88 and completes the clamp assembly 86. The clamp 91 is moved to the closed position on the tubular member 88 at such time as all elongate elements have been removed from passage 89, to prevent the flow of blood from the introducer catheter.

The guiding catheter 78 consists a flexible elongate tubular member 94. The guiding catheter 78 can be of a suitable size, as for example 5.0 French and has a length of 110 centimeters and a flow passage 96 with a diameter of 0.044". A male Luer fitting 97 with stopcock is mounted on the proximal extremity 98 of the flexible elongate tubular member 94 which is also provided with a distal extremity 99. As can be seen from the drawings, the flexible tubular member 94 has a length which is great enough so that the distal extremity 99 can extend out of the distal extremity of the introducer catheter 77. The fitting 97 has rotatably mounted thereon a threaded hub 101 which is adapted to mate with the female Luer fitting 92 carried by the clamp assembly extension tubular member 88 so that the guiding catheter 78 can be remained engaged with the clamp assembly 86. A stopcock 102 is formed integral with the fitting 97 and is provided with a handle 103 for moving it between open and closed positions with respect to the passage 96 in the flexible elongate tubular member 94. The stopcock 102 is provided with a female Luer fitting 104 which is adapted to mate with a male Luer fitting 105 carried by a conventional sidearm adapter 106. The sidearm adapter 106 is provided with central arm 107 and a sidearm 108. A hemostatic valve 109 of a conventional type is mounted on the central arm 107 and is adapted to have the guide wire 71 extend therethrough and is adapted to make a seal therewith so that blood cannot flow out of the vessel through the valve 109. A stopcock assembly 111 is mounted on the sidearm 108. It is provided with a male Luer-type fitting 112 which engages the female Luer fitting 113 provided on the side arm 108. It is provided with a handle 114 for moving the valve between opened and closed positions and a female Luer fitting 115.

With the guiding catheter 78 of the type hereinbefore described disposed within the introducer catheter 77 also hereinbefore described and having the distal extremity of the guiding catheter 78 extending beyond the distal extremity 86 of the introducer catheter 77, the distal extremity 99 is positioned over the guide wire 71 and then advanced through the sheath over the guide wire. The entire catheter assembly 76 is advanced at the same time with the guiding catheter 78 within the introducer catheter 77 until the distal extremity of the guiding catheter 78 reaches the desired site determined by the previously positioned guide wire 71.

As soon as the distal extremity 99 is in the proper position, the 0.038" guide wire 71 is withdrawn and a smaller guide wire, typically 0.016" or 0.014" guide wire 116 having a distal extremity 117 is inserted into a central arm 107 of the sidearm adapter 106 and through the lumen or passage 96 of the flexible elongate tubular member 94 of the guiding catheter 78. The guide wire 116 is advanced so that it extends slightly beyond the distal extremity 99 of the guiding catheter 78. At this juncture, the guiding catheter 78 is removed over the guide wire 116 leaving the introducer catheter 77 with clamp assembly 86 in place.

A coil delivery catheter 121 is then utilized and is advanced over the small guide wire 116 until it reaches the desired location or site. The coil delivery catheter 121 as shown in FIG. 9 consists of a flexible elongate tapered tubular member 122 having a proximal extremity 123 and a distal extremity 124. It is provided with a flow passage 126 having a suitable inside diameter, as for example 0.021" and the tapered tubular member 122 having an outside diameter of 0.028" at distal extremity 124 and an outside diameter of 0.039" at proximal extremity 123.

A female Luer-type hub 131 is mounted on the proximal extremity 123 of the flexible elongate tapered tubular member 122. The female Luer-type hub 131 is provided with a conical recess 133 which has a distal extremity 134 with a diameter approximately the diameter of the passage 126, as for example a diameter of 0.020"–0.023". The conical recess 135 is inclined from the horizontal as viewed in FIG. 10 by a suitable angle, as for example 6.52°, and has a suitable length, as for example approximately 0.585". The conical recess 135 adjoins a conical recess 133 which subtends an angle from the horizontal of approximately 2°. The conical recess 133 has a suitable length, as for example 0.200". The hub 131 is provided with a tubular strain relief portion 133a.

As soon as this delivery catheter 121 has been advanced to the desired location or site over the small guide wire 116, the small guide wire 116 is removed.

The sidearm 106 can be utilized for the heparin-saline drip to keep the blood flushed out of the introducer catheter 77.

A sidearm adapter 136 is provided which has a central arm 137 and a sidearm 138. It is provided with a male Luer fitting 139 which is threaded onto the female hub 131. A hemostatic valve 141 is provided on the central arm 137 and a stopcock 142 is provided on the sidearm 138 and has a handle 143 for moving the stopcock between opened and closed positions. The stopcock 142 is also provided with a male fitting adapted to mate with the female fitting provided on the sidearm 138. It also provided with a female-type Luer fitting 146.

When the delivery catheter 121 is advanced over the wire 116 to the desired location, the valve 109 can be tightened to prevent blood flowing from between the delivery catheter 121 and the sidearm adapter 107. The valve 141 can also be tightened to prevent the flow of blood between the guide wire 116 and sidearm adapter 136.

Once the delivery catheter 121 has its distal extremity 124 at the desired location, the valve 141 can be loosened slightly and the guide wire 116 can be removed. Thereafter, the sidearm assembly 136 can be removed. The sidearm may be removed or left attached. The cartridge 41 will pass through the valve 141 when sufficiently opened.

Figure 10:
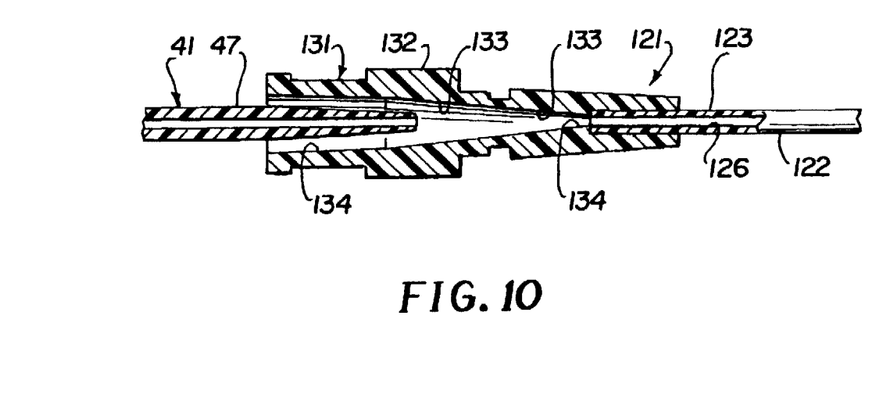
FIG. 10 is a partial cross sectional view showing the manner in which the distal extremity of the introducer cartridge is introduced into the hub of the delivery catheter.

The introducer cartridge 41 is then taken with the embolization device within the same and is pushed into the hub 131 to frictionally lodge it in the same by having its tapered extremity 48 engaging the conical recess 133 of the female hub 131. By pressing introducer cartridge 41 within the hub, the introducer cartridge is frictionally retained within the hub to hold it in place.

The stylet 61 is then taken and is advanced into the hub 51 and into the passage 43 and engages the embolization device 11 therein and is used to push it out of the introducer cartridge 41 into the passage 126 in the flexible elongate member 122 of the delivery catheter 121. The advancement of the embolization device 11 can be readily observed because of the transparency of the introducer cartridge 41 and the hub 131. As soon as the stylet 61 has advanced the embolization device 11 into the passage 126 as far as it can be advanced by the stylet 61, the stylet 61 is removed. The small guide wire 116 is then taken and its proximal end, which is the stiffer end, is introduced into the hub 131 and into the passage 126 to engage the embolization device 11 and to push the embolization device 11 through the delivery catheter 121 until the embolization device 11 is near the distal extremity 124. Typically, the embolization device will be from 50 to 75 centimeters from the proximal end of the delivery catheter 121 at this point. Thereafter, the small guide wire 116 is withdrawn and is reversed with its more flexible distal extremity 124 advanced into the hub 131 and into the passage 126 until it again engages the embolization device 11. The guide wire 116 is then pushed while being viewed under fluoroscopy until the embolization device 11 exits from the tip of the delivery catheter 121. As soon as the embolization device 11 has exited from the passage 126, it will then assume its normal C-shape and engage the walls of the vessel in which it is disposed. Its tufts 33 (see FIG. 2) carried thereby will come into contact with the blood in the vessel.

It should be appreciated that, if desired, additional embolization devices 11 can be placed in the same vessel at the same location in a similar manner by utilizing a introducer cartridge and mounting the same in the hub 131 after the other introducing cartridge has been removed.

After the desired number of embolization devices 11 have been positioned at the desired location, the sidearm 136 can be removed and a contrast agent, as for example a radiopaque dye can be introduced directly into the delivery catheter 121 to visualize directly the blood flow and the degree of embolization which is occurring. When the degree of embolization is satisfactory, the delivery catheter 121 can be removed followed by removal of the introducer catheter 77. The femoral sheath can then be removed and the opening to the femoral artery can be sutured and, if desired, alternatively it can be temporarily closed by a conventional femoral artery closure (not shown). This makes it possible to perform another embolization procedure if that proves to be necessary to achieve the desired embolism in the vessel of interest.

It is apparent from the foregoing that there has been provided an introducer cartridge and an apparatus which includes an embolization device cartridge and a method for delivering the embolization device to the desired location in a vessel of a patient. The embolization device in the form of a coil has the fibers or filaments attached to the same so that they cannot be accidentally removed from the coil. The coil has a relatively smooth outer surface which does not have lumps or bumps which would be created by tying knots into the fibers to fasten the same to the coil. In addition, there has been provided an introducer cartridge which frictionally engages the hub of the delivery catheter so that it cannot accidentally fall out. The introducer cartridge has been formed of a transparent material as has the hub of the delivery catheter so that the movement of the embolization device within and from the cartridge can be readily observed.

Another embodiment of an introducer cartridge incorporating the present is shown in FIGS. 11–14. As shown therein, the introducer cartridge 151 consists of a flexible but semi-rigid elongate tubular member 152 formed of a suitable clear plastic material such a gamma ray sterilizable plastic such as polycarbonate HPS6-1124. The tubular member 152 is provided with proximal and distal extremities 153 and 154. It is also provided with a flow passage 156 which extends from the proximal extremity to the distal extremity. The tubular member 152 can have a suitable size, as for example an outside diameter of 0.060" and an inside diameter of 0.023". The tubular member 152 can have a suitable length, as for example 4.13". The distal extremity 154 is provided with a tapered tip 161 which is shown in detail in FIG. 14 and has its outermost distal extremity provided with a suitable outside diameter, as for example 0.030" that has a taper toward the tip of approximately 3.0°. The taper from the distal extremity of the tip 161 can extend proximally for a suitable distance, as for example approximately 0.31". The distal extremity of the tip 161 has been rounded (as shown) so that there are no flashing present. The tip 161 herein described is also capable of being used with other commercially available delivery catheters which are compatible for use with 0.018" guide wires.

Figure 11:
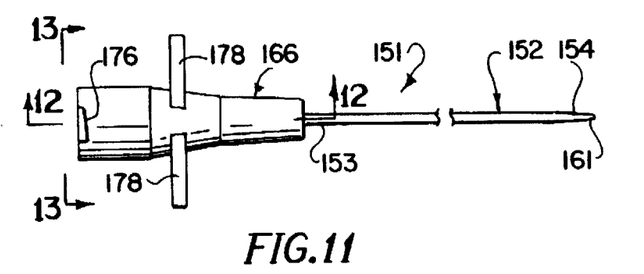
FIG. 11 is an enlarged side elevational view of another embodiment of an introducer cartridge incorporating the present invention.

The introducer cartridge 151 also includes a hub 166 which is mounted on the proximal extremity 153 of the tubular member 152. The hub 166 is also formed of a transparent plastic such as a gamma ray sterilizable polycarbonate HPS1-1124.

Figures 12, 17:
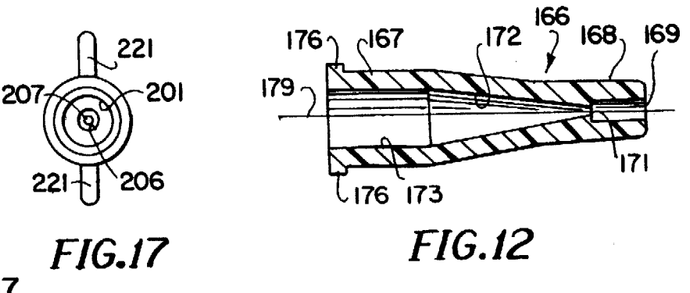
FIG. 12 is an enlarged cross-sectional view of the hub of the introducer cartridge taken along the line 12—12 of FIG. 11.
FIG. 17 is an end elevational view taken along the line 17—17 of FIG. 16.

The hub 166 is provided with proximal and distal extremities 167 and 168 with a tapered outer surface extending therebetween. The distal extremity 168 is provided with a bore 169 of a suitable size which is adapted to receive the proximal extremity of the tubular member 152, as for example a diameter of 0.062" and a length of 0.15". The bore 169 opens into an orifice 171 which can have a suitable diameter such as 0.020" which opens into a tapered passage 172 which can have a suitable length, as for example 0.455" and with a taper of approximately 8.5°. The passage 172 opens into a larger tapered passage 173 having a suitable length, as for example 0.3" with a taper of 1°. Thread lugs 176 are mounted on the exterior surface of the proximal extremity 167 and are provided with a conventional female Luer taper.

Figure 13:
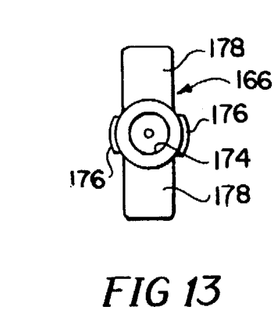
FIG. 13 is an enlarged elevational view looking along the line 13—13 of FIG. 11.
Figure 14:
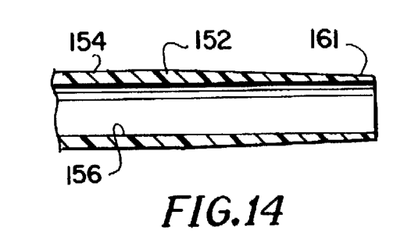
FIG. 14 is an enlarged cross-sectional view of the distal extremity of the introducer cartridge shown in FIG. 11.

The hub 166 also includes a pair of diametrically extending wings 178 which are disposed in a plane which is perpendicular to a longitudinal axis 179 extending through the hub 166. The wings 178 have a suitable length, as for example 0.320" perpendicular to the axis 179 and can have a suitable width, as for example 0.2" and a suitable thickness of 0.060". As shown, the wings 178 are positioned approximately equidistant between the proximal and distal extremities 167 and 168 of the hub and are positioned in such a manner so as to interfere as little as possible with viewing of the passages 172 and 173 in the hub 166 for a reason hereinafter explained.

The conical or tapered passage 172 has a distal extremity which has a diameter which is slightly less than the diameter of the flow passage 156 in the flexible elongate tubular member 152. Thus, as hereinbefore explained, the orifice 171 has a diameter of 0.020" which is slightly less than the inside diameter of 0.023" of the elongate tubular member 152.

Figure 15:
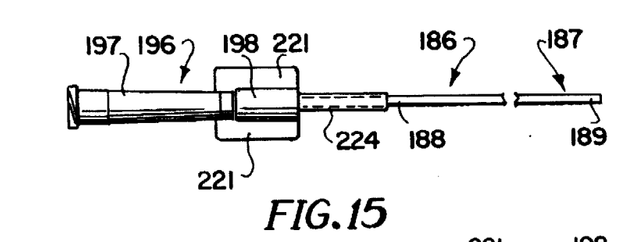
FIG. 15 is a side elevational view of a delivery catheter incorporating the present invention.
Figure 16:
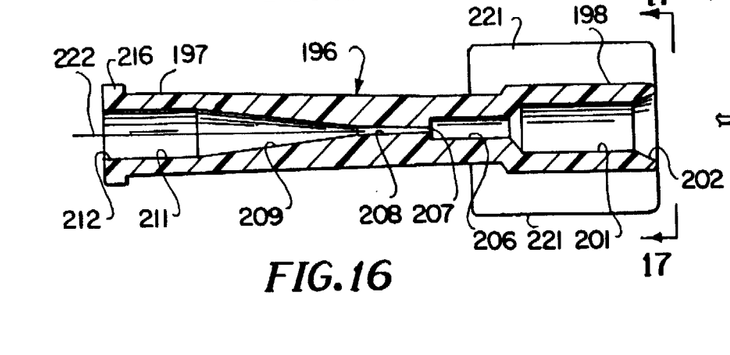
FIG. 16 is an enlarged cross-sectional view of the hub of the delivery catheter as shown in FIG. 15.

Another embodiment of the delivery catheter incorporating the present invention is shown in FIGS. 15–17. This delivery catheter 186 consists of a flexible elongate tubular member 187 having proximal and distal extremities 188 and 189. The tubular member 187 is conventional and can have a suitable outside diameter, as for example 0.028" to 0.060" and a suitable length, as for example 150 centimeters. If desired it can be formed of an opaque plastic. It is provided with a passage 191 which extends from the proximal extremity 188 to the distal extremity 189 and has a diameter such as the 0.019" to 0.023" diameter hereinbefore described.

The delivery catheter 186 also includes a hub 196 which is mounted on the proximal extremity 188 of the tubular member 187. The hub 196 is provided with proximal and distal extremities 197 and 198. The hub 196 can be formed of a clear plastic material, as for example rigid polycarbonate. The distal extremity 198 is provided with a bore 201 of a suitable size, as for example 0.145" which opens through a chamfered surface 202 having a suitable angle, as for example an angle of 12°. The bore 201 can have a suitable length, as for example from 0.466" and opens into a smaller bore 206 of a suitable diameter, as for example 0.067" to 0.079" which opens into an orifice 207 of a suitable size, as for example 0.026". The orifice 207 opens into a conical recess 208 of a suitable length, as for example a length of 0.200" and having a taper of 2.0°. The conical recess 208 opens into another conical recess 209 which has a suitable length, as for example 0.516" and a taper of 6.4°. The conical recess 209 opens into a still larger conical recess 211 having a suitable length, as for example 0.250" and having a taper of 1.6°. The recess 211 opens through an opening 212 in the proximal extremity. A conventional female Luer fitting 216 is provided on the proximal extremity 197.

The hub 196 also includes a pair of diametrically extending wings 221 which lie in a plane which is coincident with the longitudinal axis 222 of the hub 196. As shown particularly in FIG. 16, the wings 221 are positioned at the distal extremity away from the conical recesses 208, 209 and 211 so that the conical recesses can be readily viewed without the wings 221 obscuring the vision. The wings can have a suitable length, as for example 0.616" and can have a thickness of 0.060". Strain relief tubing 224 is provided on the proximal extremity 188 of the tubular member 187.

Figure 18:
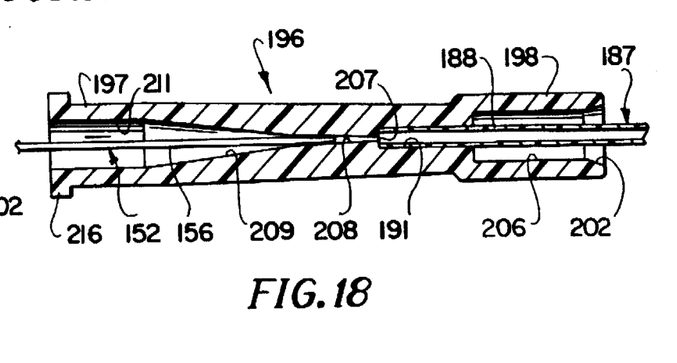
FIG. 18 is a cross-sectional view showing mating of the introducer cartridge with the delivery catheter.

In FIG. 18, the manner in which the introducer cartridge 151 mates with the delivery catheter 186 is shown. As shown, the tip 161 of the introducer cartridge 151 wedges at the transition between the conical recesses 208 and 209 although the tip 161 extends beyond this point into the conical recess 208. Thus it can be seen that the wedging between the tip 161 occurs at a point which is proximal from the distalmost extremity of the tip 161. This helps to ensure that the distalmost extremity of the tip 161 where it is the thinnest and most fragile will not accidentally break off or be damaged when the introducer cartridge 151 is inserted into the delivery catheter 186. This wedging action occurs because the taper on the tip 161 is slightly greater than the taper of the conical recess 208. While it is desirable to achieve this wedging action, it is still desirable to have the distal extremity of the tip 161 be as close as possible to the orifice 207 so that when an embolization device such as a coil hereinbefore describe exits from the introducer cartridge it will not have any opportunity to curl because it is being introduced into a very small space represented by the distal extremity of the conical recess 208 before it is introduced into the passage 191 of the elongate tubular member 187 of the delivery catheter 186.

Thus it can be seen from the construction of the introducer catheter 151 shown in FIGS. 11–14 and the construction of the delivery catheter shown in FIGS. 15–17 there are no abrupt transitions permitting the embolization coil to be readily advanced from the introducer cartridge 151 into the delivery catheter in the manner hereinbefore described. Because of the transparency of the introducer cartridge which includes a transparent hub 166 as well as a transparent tubular member 152, the position of the embolization device can always be observed visually before and during placement of the embolization device. The wings 178 have been positioned so that they obscure as little as possible of the visibility of the conical recesses 172 and 173 in the hub 166. Generally, the flexible elongate tubular member 152 is transparent so that the movement of the embolization coil can be visualized as it travels through the passage 156. This visualization can be continued even though the introducer cartridge 151 is positioned in the hub 196 of a delivery catheter 186 as shown in FIG. 18 because the hub 196 is also transparent. The wings 221 do not obscure this viewing of the embolization device during the time that it is being advanced through the hub 196 and being advanced into the tubular member 187 of the delivery catheter. The wings 221 are provided on the distal extremity of the hub 196 and for that reason they are out of the way and do not impair viewing of the movement of the embolization device from the introducer cartridge 151 into the tubular member 186. The wings 178 on the introducer cartridge 151 are positioned in such a manner so as to discourage rotation of the introducer cartridge 151 which possibly could cause damage or cause destruction of the tip 161 when the introducer cartridge 151 is positioned in the delivery catheter. The mounting of the wings 178 in a plane perpendicular to the axis of movement facilitates pushing of the introducer cartridge 151 into the delivery catheter 186 so that the desired wedging action can occur. Separation can readily be accomplished by pulling proximally on the wings 178. Similarly, the wings 221 on the delivery catheter 186 are positioned to facilitate rotation of the hub 196 of the delivery catheter which may be desirable during introduction of the delivery catheter 186.

What is claimed is:

1. In combination, an introducer cartridge and an embolization device for use with a delivery catheter having a proximal end with a hub mounted thereon and having a conical recess therein, said introducer cartridge comprising a flexible elongate tubular member formed of a plastic and having a flow passage extending therethrough and having proximal and distal extremities, said flow passage having a diameter, said distal extremity being tapered and a hub formed of plastic secured to the proximal extremity of the flexible elongate tubular member, said hub of the introducer cartridge having a conical recess free of obstructions therein with a proximal extremity and with a distal extremity, the distal extremity of the conical recess terminating at the proximal extremity of the flexible elongate tubular member and having a diameter which is less than the diameter of the flow passage in the flexible elongate tubular member to aid in preventing the embolization device from hanging up in the introducer cartridge and to prevent damage to the embolization device and, said embolization device comprising an elongate coil having a plurality of turns formed of a metal, said embolization device being situated within said introducer cartridge flow passage.

2. In combination, an introducer cartridge and an embolization device for use with a delivery catheter having a proximal end with a hub mounted thereon and having a conical recess therein, said introducer cartridge comprising a flexible elongate tubular member formed of a plastic and having a flow passage extending therethrough and having proximal and distal extremities, said flow passage having a diameter, said distal extremity being tapered and a hub formed of plastic secured to the proximal extremity of the flexible elongate tubular member, said hub of the introducer cartridge having a conical recess free of obstructions therein with a proximal extremity and with a distal extremity, the distal extremity of the conical recess terminating at the proximal extremity of the flexible elongate tubular member and having a diameter which corresponds generally to the diameter of the flow passage in the flexible elongate tubular member to aid in preventing the embolization device from hanging up in the introducer cartridge and to prevent damage to the embolization device and, said embolization device comprising an elongate coil having a plurality of turns formed of a metal, said embolization device being situated within said introducer cartridge flow passage.

3. The combination of claim 1 wherein said flexible elongate tubular member is formed of a clear plastic.

4. The combination of claim 2 wherein the introducer cartridge flexible elongate tubular member is formed of a clear plastic.

* * * * *